United States Patent [19]

Weinshenker et al.

[11] 4,054,676
[45] Oct. 18, 1977

[54] EDIBLE WITH POLYMERIC HYDROQUINONE ANTIOXIDANT

[75] Inventors: Ned M. Weinshenker, Palo Alto; James A. Dale, Redwood City, both of Calif.

[73] Assignee: Dynapol, Palo Alto, Calif.

[21] Appl. No.: 529,325

[22] Filed: Dec. 4, 1974

[51] Int. Cl.² ............................................. A23D 5/04
[52] U.S. Cl. ................................... 426/546; 252/404; 260/619 R; 260/45.95 E
[58] Field of Search ............... 260/619 R, 45.95 E, 260/62; 426/546; 252/404

[56] References Cited

U.S. PATENT DOCUMENTS

| | | | |
|---|---|---|---|
| 2,636,905 | 4/1953 | Kehe et al. | 260/62 X |
| 2,670,340 | 2/1954 | Kehe | 260/619 R UX |
| 2,700,029 | 1/1955 | Cassidy | 260/62 X |
| 2,801,981 | 8/1957 | Spacht et al. | 260/45.95 E X |
| 2,832,806 | 4/1958 | Zerbe | 260/619 R X |
| 3,062,895 | 11/1962 | Martin et al. | 260/619 R |
| 3,424,821 | 1/1969 | Hunter | 426/546 X |

FOREIGN PATENT DOCUMENTS 695,887   10/1964   Canada .................................. 260/62

Primary Examiner—Joseph M. Golian
Attorney, Agent, or Firm—William H. Benz

[57] ABSTRACT

Polymeric hydroquinones of the structure

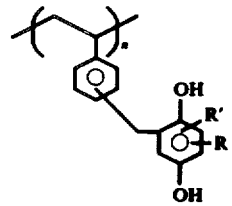

, wherein $n$ is from 3 to 10,000 inclusive and R and R' independently are hydrogen or a lower alkyl, are disclosed, as is the preparation and the use of such materials, especially as nonabsorbable polymeric antioxidants for edible materials.

5 Claims, No Drawings

EDIBLE WITH POLYMERIC HYDROQUINONE ANTIOXIDANT

BACKGROUND OF THE INVENTION

1. Field of the Invention

This invention relates to polymeric hydroquinones which are especially useful as antioxidants in edible materials such as foods.

2. The Prior Art

The prevention or reduction of oxidation is important to the quality and life of a wide range of materials such as plastics and rubbers. Oxidation is an especial problem with consumable (edible) materials, as such oxidation not only can destroy desirable nutritional values in these materials, but also can render these materials unpalatable and unfit for consumption. A variety of materials have been proposed as additives to inhibit undesired oxidation. A common class of such materials have a phenolic or hydroquinolic structure. BHA (butylated hydroxy anisole) and BHT (butylated hydroxy toluene) are two of the most commonly employed antioxidants in edible compositions. While BHA and BHT have never been proven to be significantly toxic, allergenic responses have been observed and their use in foods has often been opposed. Upon ingestion with food, they pass through the gastrointestinal tract walls into the systemic circulation where they are metabolized into products whose identity and safety are not proven.

It has been proposed by Alejandro Zaffaroni, in his United States patent application Ser. No. 367,971, now U.S. Pat. No. 3,994,828, to avoid these toxicity questions of conventional antioxidants by fixing the antioxidant moieties to a controller molecule which is of a size which precludes its passage through the walls of the gastrointestinal tract. Such an approach does work and it is possible to essentially completely prevent the passage of antioxidant moieties into the systemic circulation by incorporating them into nonabsorbably-large molecules. This technique has additional benefits in that the antioxidant molecules, being large, are not susceptible to undesired movement — either migration in a substrate or volatilization from a substrate, benefits which substantially improve their usefulness not only in foods but also in non-food applications.

A substantial number of these polymeric antioxidants have been prepared. Some are similar in antioxidant activity to the conventionally used monomeric BHA and BHT materials, but as a rule, they were not markedly superior in their antioxidant activity to these prior materials.

Knowing from the art that the hydroquinones are an attractive family of antioxidants, various polymeric hydroquinone antioxidants were investigated.

Materials having a structure

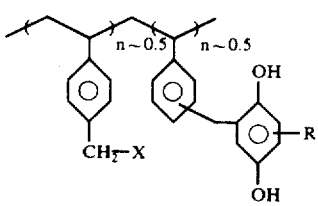

wherein X is a leaving group and R is a lower alkyl, were prepared by reacting poly(X-methyl styrene) with the required hydroquinone in the presence of a cationic catalyst. These materials were of relatively unimpressive antioxidant activity. Further study of this reaction scheme failed to yield materials of antioxidant activity higher than that observed with conventional monomeric BHA and BHT.

It is thus a primary object of this invention to provide to the art a polymeric hydroquinone antioxidant with a molecular size suitable for substantial nonabsorbtivity from the gastrointestinal tract and antioxidant activity superior to conventional BHA and BHT antioxidants.

STATEMENT OF THE INVENTION

A group of new high activity hydroquinone antioxidants has now been found. These materials are polymeric and have a structure represented by General Structural Formula I,

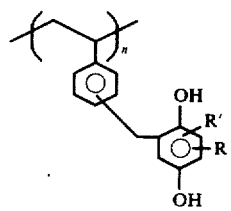

wherein R and R' independently are hydrogen or lower saturated alkyl of from 1 to 5 carbon atoms, and $n$ has a value of from 3 to 10,000 inclusive. These materials preferably consist essentially of $n$

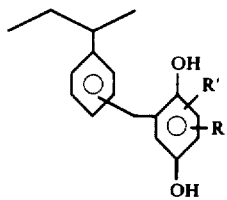

units, containing not more than about 5% of inadvertantly incorporated other polymeric units. These materials are prepared directly from monomeric vinylbenzyl compounds containing a leaving group (such as vinylbenzylchloride) and an R and R'-substituted hydroquinone by intimately contracting these reactants in liquid phase in the presence of a cationic catalyst (such as zinc chloride) at a moderate temperature (10° to 100° C) for from 0.2 to 5 hours. These materials act with high activity as antioxidants for plastics, rubbers, oils, and especially edible materials such as foodstuffs. In the last application they offer the advantage of being substantially nonabsorbable and hence nontoxic.

DETAILED DESCRIPTION OF THE INVENTION

The Hydroquinone Products

The hydroquinone products of this invention are structurally depicted by General Structural Formula I. They are polymers, each link of which comprises a hydroquinone or a mono- or di-alkylhydroquinone group joined through a methylenic bridge to an aromatic carbon of an ethylbenzene group. The ethylbenzene groups form the required polymer through their ethyl groups.

The hydroquinone group may be hydroquinone itself or it may be a mono- or di(lower saturated alkyl)hydroquinone. The lower saturated alkyls should have from 1 to 5 carbon atoms and thus include methyl; ethyl; n- and isopropyls; n-, iso-, and t-butyls; and the several amyls. As examples of typical useful hydroquinones may be mentioned hydroquinone, methylhydroquinone, 2,3- 2,5- and 2,6-dimethylhydroquinone, ethylhydroquinone, 2-ethyl-5-isopropylhydroquinone, isopropylhydroquinone, t-butylhydroquinone and 2-t-butyl-6-methylhydroquinone. Preferred among the hydroquinones are hydroquinone and the mono(lower saturated alkyl)hydroquinones wherein the alkyl has from 1 to 5 carbons inclusive. Hydroquinone, methylhydroquinone, ethylhydroquinone, isopropylhydroquinone, and t-butylhydroquinone make up a group of more preferred hydroquinones while t-butylhydroquinone is the most preferred hydroquinone.

In the finished polymer, the hydroquinone group is linked through a methylene bridge to an aromatic ring. Also attached to the aromatic ring is an ethylene moiety. This ethylene moiety is part of an alkyl polymer chain. This chain is made up of covalent carbon-carbon bonds. These bonds are relatively nonmetabolizable and nonrupturable. This ensures that the polymer molecule will hold together in use and not break down into individual groups. The polymer, as depicted by General Structural Formula I, is made up of $n$ linked together groups. $n$ Has a value which may vary from 3 to 10,000. While materials in which $n$ equals 1 or 2 are believed to be new and to have antioxidant activity, their small molecular size can lead to absorption from the gastrointestinal tract when used in food as well as undesired migration and volatility during processing. $n$ Can, if desired, have a value greater than 10,000, but materials of such large size are not required either for nonabsorbtivity or for nonvolatility.

Preferably, $n$ has a value of from about 4 to about 4000 inclusive, very preferably from 5 to 2000 inclusive, most preferably from 5 to 750.

Use of the Materials as Antioxidants

The present materials are useful as antioxidants. When they are admixed with oxidizable substances such as plastics, rubbers, or deterioration-prone foodstuffs in an amount of from about 2 to 50,000 parts per million by weight (basis oxidizable substance), they function to retard oxidation of the substance. In rubbers and plastics these materials offer the advantage of being substantially nonvolatile and thus unlikely to be lost by vaporization. They are also less likely to migrate through these substrates. In oxidizable consumables, as exemplified by food products and food components such as edible oils, fats, essential oils, nuts and flavorings, an effective amount of these antioxidant materials such as from 2 to 10,000 parts per million by weight or preferably from 5 to 1000 parts per million by weight, is generally employed. In such use, the high molecular weight and concomitant low migration and volatility greatly enhance product processing such as by reducing steam distillation of the antioxidants, and eliminating the need to continually add additional antioxidant to compensate for such loss. Also, the antioxidants of this invention present the advantage of nonabsorbtivity through the walls of the gastrointestinal tract, thereby eliminating any risk of toxicity.

When used as antioxidants for oxidizable substances, these materials are intimately admixed with the oxidizable substance such as being dissolved in the oxidizable substance, by being mixed as solid particles through the oxidizable substance, by being added as a solution in a suitable carrier, or the like.

Preparation of the Materials

The hydroquinone materials of this invention are polymers. Generally they are suitably prepared directly from a vinylbenzyl compound and a hydroquinone without a separate isolation of the intermediate vinylbenzylhydroquinone monomer. Such a process may be carried out by forming an intimate mixture of the benzyl compound and the hydroquinone in an organic reaction solvent in the presence of a cationic catalyst and maintaining the mixture at a temperature of from about 10° to about 200° C for from 0.2 hours to about 15 hours and thereafter isolating the desired polymer product from the reaction solvent and catalyst.

The feedstocks for this preparation are vinylbenzyl compounds which contain a leaving group and are suitable for forming benzyl cations, and R and R'-substituted hydroquinones. The most common and preferred vinylbenzyl compound is vinylbenzylchloride. Other useful and preferred materials include the remaining vinylbenzylhalides, i.e., vinylbenzylflouride, vinylbenzyliodide, and vinylbenzylbromide; sulfur-containing vinylbenzyl materials such as vinylbenzylsulfonate, vinylbenzylsulfate, the vinylbenzylhalosulfites, vinylbenzylsulfite, and the half ester forms of vinylbenzylsulfuric acid and vinylbenzylphosphoric acid may also be employed.

In the R and R'-substituted hydroquinones, R and R' independently may equal hydrogen or a lower alkyl of from 1 to 5 carbon atoms. R and R' are described in more detail hereinabove. If desired, of course, mixtures of two or more vinylbenzyl compounds and/or hydroquinones may be employed.

The benzyl compound and hydroquinone are combined in an organic reaction solvent. Suitable solvents may be characterized as liquid organic inert aprotic solvents and include ethers such as diethyl ether and glyme; and halohydrocarbons such as dichloroethane or trichloroethane. Blends of these materials may be used as well. For ease of use and economy, diethylether and 1,2-dichloroethane and mixtures thereof are preferred solvents.

The relative amounts of the two reactants and the solvent should be chosen within the following limits: the molar ratio of hydroquinone to vinylbenzyl compound employed should be between 2:1 to 1:2. Preferably, this ratio ranges between 1:11 to 1:1.01. For good reaction, the amount of solvent should be such as to permit the total concentration of hydroquinone and vinylbenzyl compound to be from about 60 to about 5 percent by weight based on the total solution weight. Preferably this concentration is maintained between 40 and 20 percent by weight. Control of solvent amount to provide reactant concentrations within these ranges permits smooth and trouble-free polymerization.

The reaction is carried out at a moderate temperature such as about 10° C or higher. A maximum temperature of about 100° C preferably should be observed. Best results are obtained at temperatures of from about 15° to about 75° C. Reaction times will vary inversly with temperature and preferably will range between about 0.5 hours and 12 hours. Depending upon the temperature desired, it may be necessary to carry out the reaction under elevated pressure so as to maintain the solvent in liquid phase. Other than for this reason, no elevated pressure need be employed.

A catalyst should be present in the reaction mixture. Suitable catalysts are cationic catalysts. This class of catalysts is represented by transition metal halides such as $AlCl_3$, $ZnCl_2$ $SnCl_4$, $FeCl_3$, $SbCl_3$, $SbCl_5$, $BF_3$, $BF_3$-etherate, $TiCl_4$, $BCl_3$, $MgCl_2$ and $CdCl_2$. A preferred group of catalysts are $ZnCl_2$ and $MgCl_2$, with $ZnCl_2$ being a most preferred catalyst. A catalytically effective amount of catalyst is employed, which amount may be defined as generally falling in the range of from about 0.2 to about 3.0 moles per mole of vinylbenzyl compound. Preferably from 0.5 to 1.2 moles of catalyst per mole of vinylbenzyl compound is employed.

During the reaction, it is desirable to supply agitation to assure thorough contact of the reactants and the catalyst.

Following the reaction, it is necessary to isolate the polymer product from the reaction catalyst and often desirable to isolate the product from the reaction solvent. This isolation may be carried out, in the case of a solid catalyst system, by first straining (filtering), settling or centrifuging the solid catalyst particles from the reaction mixture and then evaporating off the reaction solvent, such as in vacuum driers or the like. Alternatively, the catalyst can be removed by extraction from the organic reaction mixture into an aqueous liquid phase.

The product polymer may be washed, if desired, to remove residual impurities and it may also be fractionated into molecular weight cuts by art-known methods, if such cuts are required for product applications or the like.

The materials of this invention, their production and their use are further illustrated in the following Examples. These are intended only to demonstrate the invention and are not to be construed as limiting its scope, which scope is instead defined by the appended claims.

EXAMPLE I

A. A three liter flask was equipped with a condenser, a thermometer, and a stirrer. Boiling chips and an argon atmosphere were added. 250 Ml of anhydrous diethyl ether was added, followed by 166.2 g of 97% pure t-butylhydroquinone (Aldrich Company), and the mixture was stirred to solution.

Next, 147.4 g of fused zinc chloride was added along with 300 ml of dichloroethane and 163 g (1.07 moles per mole of t-butylhydroquinone) of vinylbenzylchloride. The mixture was stirred. Its temperature rose to 30° C, but after adding 180 ml of dichloroethane and cooling in an ice bath, the temperature lowered to 19° C. The temperature was maintained between 19° – 30° C for two hours and then raised to 65° C (reflux temperature) and there maintained for 8 hours.

The cooled reaction mixture was diluted with ether (200 ml, distilled solvent grade) and extracted three times with approximately one liter of water. After drying with sodium sulfate and magnesium sulfate, filtering, and diluting with acetone (600 ml) to approximately two liters, the solution gave a soft taffy-like precipitate on dropping slowly into vigorously stirred hexane (7 liters). A second precipitation using approximately two liters of 1:1 acetone:THF also gave a soft taffy-like precipitate.

A third precipitation in diethylether-THF gave a chalky powder in 83% isolated yield. This product was characterized as follows:

Its molecular weight was determined using gel permeation chromatography comparison with a series of polystyrene standards of known weight range from about $2 \times 10^6$ to $1 \times 10^3$ ($n = 3$ to about 6000).

Its structure was shown to be consistent with the formula

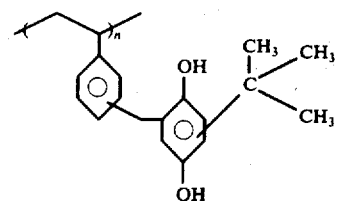

by proton and $^{13}C$ NMR analysis, oxidation potential, chlorine analysis, infrared and ultraviolet spectral analyses and acid-base titrations.

B. The product of Part A, ("A"), was tested as an antioxidant for an oxidizable substrate. The test was conducted as follows: 50 ml of substrate (freshly opened Wesson™ Oil - a blend of cottonseed and soybean oils containing no additives and packed at the site of manufacture under nitrogen) containing 0.5 ml of benzene and 10 mg of "A" (200 ppm concentration) was placed in a 6 cm diameter by 8 cm high round glass jar and placed open in a forced air draft oven maintained at 80° C. A one ml sample was taken every 10-15 hours and analyzed for peroxide content by iodometric titration.

The iodometric titration involved adding a constant amount of acetic acid — chloroform solution followed by a constant amount of potassium iodide and back titrating with sodium thiosulfate to a starch indicator endpoint in accordance with A.O.C.S. (American Oil Chemists Society) method Cd 8 - 53. It is generally regarded that peroxide content and the rate of build up of peroxides in oils are a measure of the stability of oils. The slower the rate of peroxide value increase in oils with heating - the less prone to oxidation or more stabilized the oil is. (See for example A.O.C.S. tentative method Cd 12 - 57 for more information on peroxides and food stability).

At 0 hours of heating the oil plus "A" contained 0.7 MEQ/liter of peroxide. The value increased as shown in Table I.

TABLE I

| Test Material | Hours | MEQ Peroxide/Liter | | | |
|---|---|---|---|---|---|
| | | 0 | 15 | 39 | 63 |
| Oil + 200 ppm A | | 0.7 | 1.9 | 5.1 | 9.7 |
| Plain Oil | | 1.1 | 10.2 | 31.5 | 53.4 |
| Oil + 200 ppm BHT | | 1.0 | 8.2 | 27.6 | 46.2 |
| Oil + 200 ppm BHA | | 0.8 | 7.7 | 27.4 | 45.9 |

As is also shown in Table I, 3 control samples were run for comparison purposes. Plain unstabilized Wesson ™ Oil (containing 1% benzene) and Wesson ™ Oil containing 1% benzene and 200 ppm of the common antioxidants, BHT and BHA, were also tested. These comparison tests indicated that product A had substantial antioxidant activity.

EXAMPLE II

Hydroquinone (2.2 g, 0.02 moles), zinc chloride (2.72 g 0.02 moles) and 40 ml of 1,2-dichloroethane were stirred under argon at about 24° C (room temperature) for 1 ½ hours. The mixture was heated to reflux and there maintained for 15 minutes. After cooling to room temperature, 3.06 g (0.02 moles) of vinylbenzylchloride was added along with about a ml of diethylether. After several hours at room temperature, the mixture was refluxed at 60°-64° C for 8 hours. Twenty ml of diethylether were added and the mixture was evaporated to dryness. The residue was dissolved in tetrahydrofuran and precipitated in a 1:2 methanol-water mixture. The precipitate was dissolved in tetrahydrofuran, dried and precipitated again in hexane to yield a product giving analytical results consistent with the structure

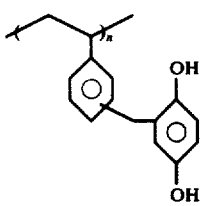

wherein n is a distribution of values from about 3 to greater than 1000.

This material, when tested for antioxidant activity by the method of Example I, is seen to have significant activity.

EXAMPLE III

The preparation of Part A of Example I was repeated seven times. Feedstock and catalyst mole ratios were varied, as were reaction temperature and reaction solvent type and amount. The changes had the effect of varying the molecular weight of the product of Example I. The reaction conditions and results are given in Table II.

prepraration, vinylbenzylbormide and 2,5-dimethylhydroquinone are employed as the reactants. Both of these preparations yield polymer products in accordance with this invention.

What is claimed is:

1. An oxidizable composition stabilized against the oxidative edible degradation comprising an oxidizable material having admixed therewith a stabilizing amount in the range of from 2 ppm to 50,000 ppm by weight of the polymeric hydroquinone represented by the structural formula

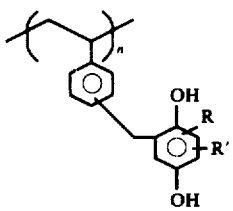

wherein R and R' are independently selected from the members of the group consisting of hydrogen and lower saturated alkyls of from 1 to 5 carbon atoms inclusive and n has a value of from 3 to 10,000 inclusive.

2. The composition of claim 1, wherein R is hydrogen and R' is selected from the members of the group consisting of hydrogen and lower saturated alkyls of from 1 to 5 carbon atoms inclusive.

3. The composition of claim 2, wherein R' is a tertiary butyl group.

4. The composition of claim 2, wherein R' is hydrogen.

TABLE II

| | Reactant Concentration Moles per liter | | | Solvent Components, Parts | | | Reaction | | Product peak molecular weight as measured by Gel permeation chromatography relative to polystyrene standards |
|---|---|---|---|---|---|---|---|---|---|
| Run Number | Vinyl benzyl chloride | t-butyl hydroquinone | Zinc chloride | Dichloroethane | Diethyl ether | Dusopropyl ether | Time hours | Temp. °C | |
| 1 | 1.00 | 1.00 | 1.02 | 1.0 | | | 12 | 26–29 | 750; 4,500; 65,000 |
| 2 | 1.02 | 1.00 | 1.00 | | | 1.0 | 4 | 12 | |
| | | | | | | | 9 | 61 | 7,000 |
| 3 | 1.02 | 1.00 | 1.00 | | | 1.0 | 8 | 12 | 700 |
| 4 | 1.01 | 1.00 | 1.20 | 2.0 | 1.0 | | 8 | 63 | 1,100 |
| 5 | 1.03 | 1.00 | 1.03 | 2.6 | 1.0 | | 1 | 67 | 8,600; 170,000 |
| 6 | 1.03 | 1.00 | 1.04 | 2.0 | 1.0 | | 2 | 12 | |
| | | | | | | | 8 | 65 | 8,800 |
| 7 | 1.03 | 1.00 | 1.04 | 2.0 | 1.0 | | 4 | 65 | 10,000; 100,000 |

EXAMPLE IV

The preparation of Example II is repeated twice with modifications. First, magnesium chloride is substituted for zinc chloride as cationic catalyst. In the second 5. The composition of claim 2, wherein n has a value of from 4 to 4000 inclusive.

* * * * *